(12) United States Patent
Hirasawa et al.

(10) Patent No.: US 8,912,192 B2
(45) Date of Patent: Dec. 16, 2014

(54) EXTENDED RELEASE PREPARATION

(75) Inventors: Noriyuki Hirasawa, Toshima-ku (JP);
Nobuyoshi Kamikido, Toshima-ku (JP);
Akihiko Tasaki, Toshima-ku (JP);
Shusei Ito, Toshima-ku (JP)

(73) Assignees: Taisho Pharmaceutical Co., Ltd, Tokyo (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/578,323

(22) PCT Filed: Feb. 10, 2011

(86) PCT No.: PCT/JP2011/052909
§ 371 (c)(1),
(2), (4) Date: Aug. 10, 2012

(87) PCT Pub. No.: WO2011/009573
PCT Pub. Date: Aug. 18, 2011

(65) Prior Publication Data
US 2012/0316177 A1 Dec. 13, 2012

(30) Foreign Application Priority Data

Feb. 12, 2010 (JP) ................................. 2010-028984

(51) Int. Cl.
| | | |
|---|---|---|
| C07D 201/00 | (2006.01) | |
| A61K 31/501 | (2006.01) | |
| A61K 9/20 | (2006.01) | |

(52) U.S. Cl.
CPC ............. *A61K 31/501* (2013.01); *A61K 9/2054* (2013.01); *A61K 9/2013* (2013.01); *A61K 9/2095* (2013.01); *A61K 9/2018* (2013.01); *A61K 9/2027* (2013.01)
USPC ............................ 514/252.03; 514/252; 514/3

(58) Field of Classification Search
None
See application file for complete search history.

(56) References Cited

U.S. PATENT DOCUMENTS

| 5,942,249 A | 8/1999 | Iwao et al. | |
|---|---|---|---|
| 6,037,346 A | * 3/2000 | Doherty, Jr. et al. | .......... 514/258 |

(Continued)

FOREIGN PATENT DOCUMENTS

| CN | 1194139 A | 9/1998 |
|---|---|---|
| EP | 0 284 849 A1 | 10/1988 |

(Continued)

OTHER PUBLICATIONS

Berge, S. M. et al., Pharmaceutical Salts, Journal of Pharmaceutical Sciences, Jan. 1977, vol. 66, No. 1, p. 1.*
SB., Sateesha, et al. Influence of Organic Acids on Diltiazem HCL Release Kinetics from Hydroxypropyl Methyl Cellulose Matrix Tablets, J. Young Pharm. vol. 2, No. 3, pp. 229-233, 2010 publication year.*

(Continued)

*Primary Examiner* — San-Ming Hui
*Assistant Examiner* — Jeanmarie Calvillo
(74) *Attorney, Agent, or Firm* — Sughrue Mion, PLLC

(57) ABSTRACT

Disclosed is a sustained release preparation which releases a poorly soluble medicinal agent in a pH-independent manner. Also disclosed is a sustained release preparation which is capable of controlling the $C_{max}$ of a medicinal agent to an adequate amount and is thus capable of maintaining the level of the medicinal agent in the blood to a level at which medicinal effects can be expected for a long period of time. Specifically disclosed is a sustained release preparation which is characterized by containing a pharmaceutically acceptable salt of 4-bromo-6-[3-(4-chlorophenyl)propoxy]-5-(3-pyridylmethylamino)-3(2H)-pyridazinone, and hypromellose. An organic acid is blended in the sustained release preparation in an amount of less than 1% by mass.

4 Claims, 9 Drawing Sheets

(56) References Cited

U.S. PATENT DOCUMENTS

| | | | |
|---|---|---|---|
| 6,656,502 | B1 | 12/2003 | Hara et al. |
| 8,057,675 | B2 * | 11/2011 | Baseeth et al. ............... 252/180 |
| 2006/0094704 | A1 * | 5/2006 | Boolell ................ 514/210.21 |
| 2009/0117190 | A1 | 5/2009 | Sato et al. |

FOREIGN PATENT DOCUMENTS

| | | |
|---|---|---|
| EP | 0 482 208 A1 | 4/1992 |
| EP | 0860169 | 8/1998 |
| EP | 1927358 A1 | 6/2008 |
| JP | 61-501511 A | 7/1986 |
| JP | 62-120315 A | 6/1987 |
| JP | 63-215620 A | 9/1988 |
| JP | 63-290818 A | 11/1988 |
| JP | 6-330524 A | 11/1994 |
| JP | 10-273440 A | 10/1998 |
| WO | 85/04100 A1 | 9/1985 |
| WO | 91/16314 A1 | 10/1991 |
| WO | 98/41210 A1 | 9/1998 |
| WO | 2007/023729 A1 | 3/2007 |

OTHER PUBLICATIONS

S. Nie, et al, The Effect of Citric Acid Added to HPMC Matrix Tablets on the Release Profile of Vinpocetine, Drug Development and Industrial Pharmacy, 2004, vol. 30, No. 6, pp. 627-635.*

Liam C. Feely et al., "The influence of polymeric excipients on drug release from hydroxypropylmethylcellulose matrices", International Journal of Pharmaceuticals, 1988, pp. 131-139, vol. 44, No. 1-3.

Sung-Hyun Park et al., "Preparation of an extended-release matrix tablet using chitosan/Carbopol interpolymer complex", International Journal of Pharmaceuticals, 2008, pp. 39-44, vol. 347, No. 1-2.

International Search Report for PCT/JP2011/052909 dated Apr. 5, 2011.

Extended Search Report issued in corresponding European Patent Application No. 11742316 on Jul. 12, 2013.

Manthena V.S. Varma et al., "Influence of micro-environmental pH on the gel layer behavior and release of a basic drug from various hydrophilic matrices", Journal of Controlled Release, 2005, 103: 499-510.

Communication for EP Application No. 11742316.0 issued Jul. 3, 2014.

* cited by examiner

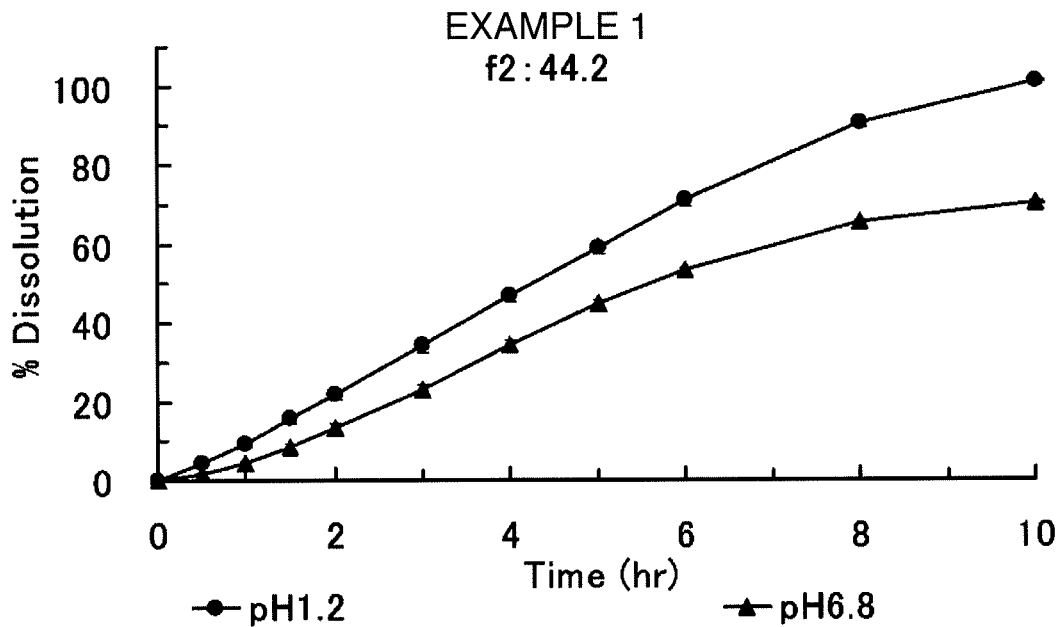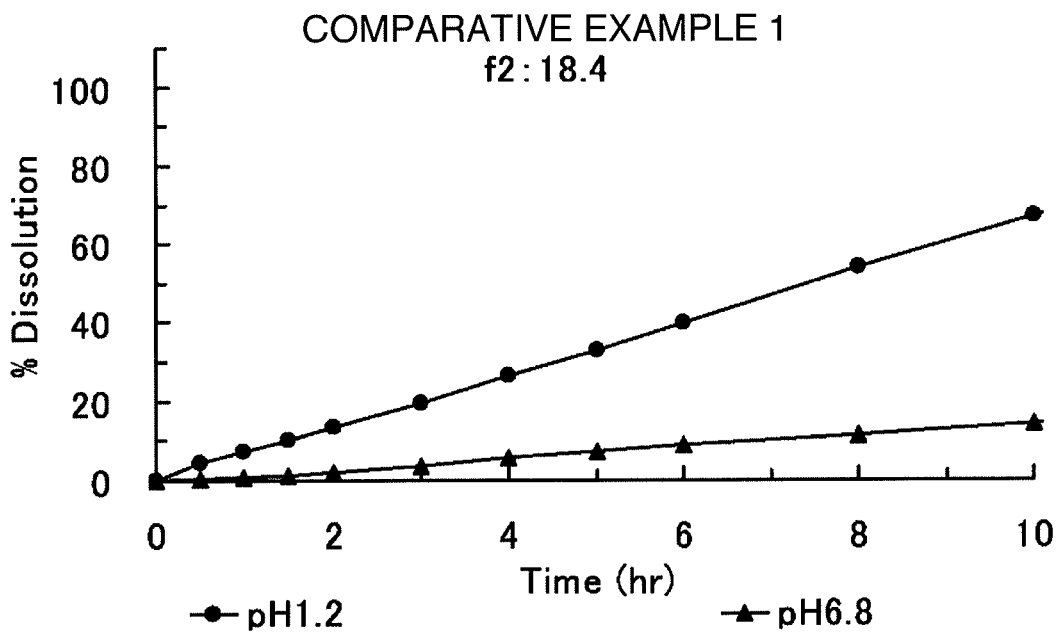

EXTENDED RELEASE PREPARATION

CROSS REFERENCE TO RELATED APPLICATIONS

This application is a National Stage of International Application No. PCT/JP2011/052909 filed Feb. 10, 2011, claiming priority based on Japanese Patent Application No. 2010-028984 filed Feb. 12, 2010, the contents of all of which are incorporated herein by reference in their entirety.

TECHNICAL FIELD

The present invention relates to a sustained release preparation which controls release of active ingredients from the preparation and achieves stable and continuous release.

BACKGROUND ART

Sustained release preparations are useful preparations which are capable of decreasing frequency of administration and controlling concentrations of medicinal agents in blood so as to maintain medicinal effects. For example, use of a sustained release preparation can decrease administration frequency of a medicinal agent such as ibuprofen (half-life period: 2 hours) or phenylpropanolamine hydrochloride (half-life period: 4 hours) from three times per day (ordinarily necessary times) to twice per day. Moreover, use of a sustained release preparation can control the concentration of a medicinal agent such as theophylline in blood, which agent is narrow in concentration range wherein medicinal effects are exerted or side effects occur, so as to attain reduction of side effects and long duration of medicinal effects. As one approach for attaining such a sustained release preparation, hydrogel bases using water soluble polymers as sustained release bases are proposed (Patent Documents 1 to 4).

4-bromo-6-[3-(4-chlorophenyl)propoxy]-5-(3-pyridylmethylamino)-3(2H)-pyridazinone (hereinafter abbreviated as "compound A") or a pharmaceutically acceptable salt thereof is a compound which has an inhibitory effect against phosphodiesterase III enzymes, and has shown great promise as a therapeutic medicine for a disease such as asthma (Patent Document 5). However, this compound is greatly influenced by first pass effect through liver and has a very short half-life period of about 1.5 hours in blood plasma. Furthermore, since it is known that phosphodiesterase III enzymes exist in many internal organs, the concentrations of the compound in blood plasma are required to be controlled appropriately so as to attain its activity and avoid occurrence of side effects simultaneously. Therefore, it is preferable that a sustained release preparation for compound A or its pharmaceutically acceptable salt lowers the maximum concentration in blood plasma ($C_{max}$) of compound A and maintains the effective concentration in blood plasma for a long period of time.

On the other hand, a pharmaceutically acceptable salt of compound A decreases its solubility in water at a pH range of about 4.0 or higher, and becomes quite poorly soluble around at a neutral pH range which is similar to enteric environment. As a result, there arise problems that a preparation containing a pharmaceutically acceptable salt of compound A is poor in dissolution after oral administration and is low in absorbability to dogs, i.e., bioavailability in a fasting state is about 10%. For improving such a poor dissolution and absorbability, it has been found that an organic acid such as citric acid, tartaric acid, malic acid, fumaric acid, malonic acid, succinic acid or maleic acid is present together with a pharmaceutically acceptable salt of compound A to obtain a preparation which attains immediate release (Patent Document 6). It has also been found that, when an organic acid such as citric acid, tartaric acid, malic acid, fumaric acid, malonic acid, succinic acid or maleic acid is present together with a pharmaceutically acceptable salt of compound A, and a hydrogel base such as a carboxyvinyl polymer is blended therewith, dissolution of compound A from the preparation can be controlled independently upon pH (Patent Document 7). However, the thus obtained preparation merely delays the time-to-maximum plasma concentration ($T_{max}$) of compound A, and is insufficient in properties required of a sustained release preparation, i.e., reduction of $C_{max}$ and maintenance of the effective concentration in blood plasma.

CITATION LIST

Patent Literature

[PATENT LITERATURE 1] JP 63-215620 A
[PATENT LITERATURE 2] JP 62-120315 A
[PATENT LITERATURE 3] WO 1998/041210
[PATENT LITERATURE 4] JP 06-330524 A
[PATENT LITERATURE 5] WO 1991/016314
[PATENT LITERATURE 6] JP 10-273440 A
[PATENT LITERATURE 7] WO 2007/023729

SUMMARY OF INVENTION

Technical Problem

It is an object of the present invention to provide a sustained release preparation which exhibits dissolution of compound A independent upon pH. It is another object of the present invention to provide a sustained release preparation which is capable of controlling $C_{max}$ of compound A to an adequate amount and is thus capable of maintaining the level of compound A in blood plasma to a level at which medicinal effects can be expected for a long period of time.

Solution to Problem

Surprisingly, the present inventors have found that the above problems can be solved by blending a pharmaceutically acceptable salt of compound A with hypromellose That is, the present invention provides the following:
(1) a sustained release preparation characterized in that the sustained release preparation contains a pharmaceutically acceptable salt of 4-bromo-6-[3-(4-chlorophenyl)propoxy]-5-(3-pyridylmethylamino)-3(2H)-pyridazinone and hypromellose, and an organic acid is contained in the sustained release preparation in an amount of less than 1% by mass;
(2) a sustained release preparation according to claim 1, characterized by further containing a pharmaceutically acceptable inert carrier;
(3) a sustained release preparation according to claim 1 or 2, characterized in that the pharmaceutically acceptable salt of 4-bromo-6-[3-(4-chlorophenyl)propoxy]-5-(3-pyridylmethylamino)-3(2H)-pyridazinone is a hydrochloride;
(4) a sustained release preparation according to any one of claims 1 to 3, characterized in that the organic acid is contained in an amount of 0.5% by mass or less based on the total preparation; or
(5) a sustained release preparation according to any one of claims 1 to 4, characterized in that the organic acid is not contained.

Advantageous Effects of Invention

The sustained release preparation of the present invention has successfully dissolved compound A independently upon pH while compound A has a solubility dependent upon pH. Moreover, when the preparation of the present invention was orally administered, $C_{max}$ of compound A was controlled to an adequate amount, and the level of compound A in blood plasma could be maintained to a level at which medicinal effects can be expected for a long period of time.

BRIEF DESCRIPTION OF DRAWINGS

FIG. 1 shows the result of the dissolution test of the sustained release preparation of Example 1 (Mean±SD, n=3).

FIG. 2 shows the result of the dissolution test of the sustained release preparation of Comparative Example 1 (Mean±SD, n=3).

DESCRIPTION OF EMBODIMENTS

Figure 3:
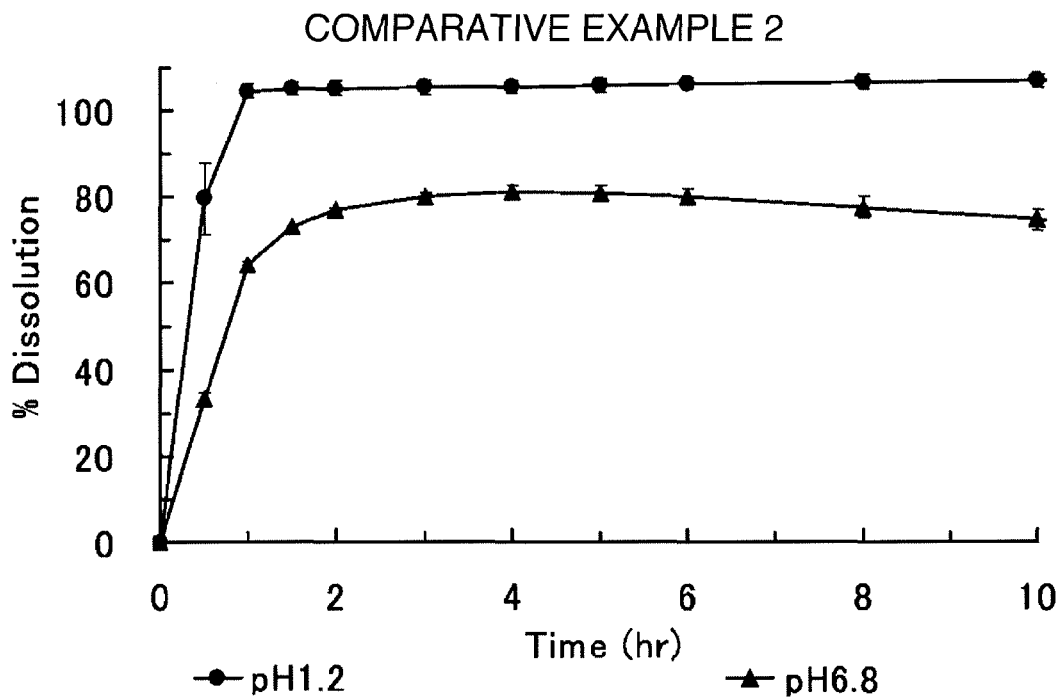
FIG. 3 shows the result of the dissolution test of the preparation of Comparative Example 2 (Mean±SD, n=3).
Figure 4:
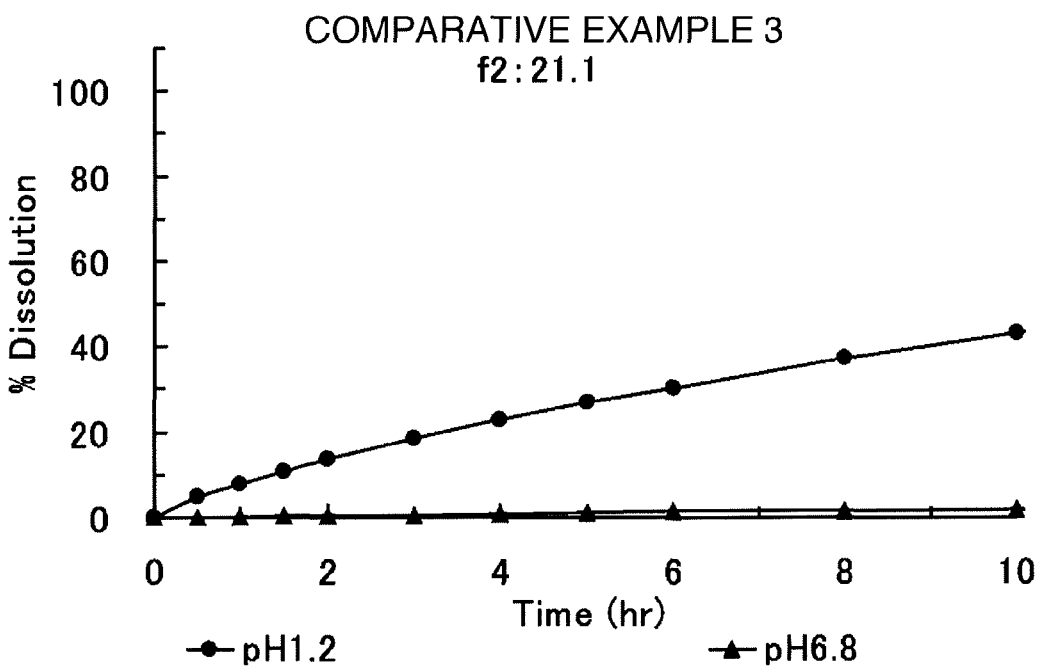
FIG. 4 shows the result of the dissolution test of the sustained release preparation of Comparative Example 3 (Mean±SD, n=3).
Figure 5:
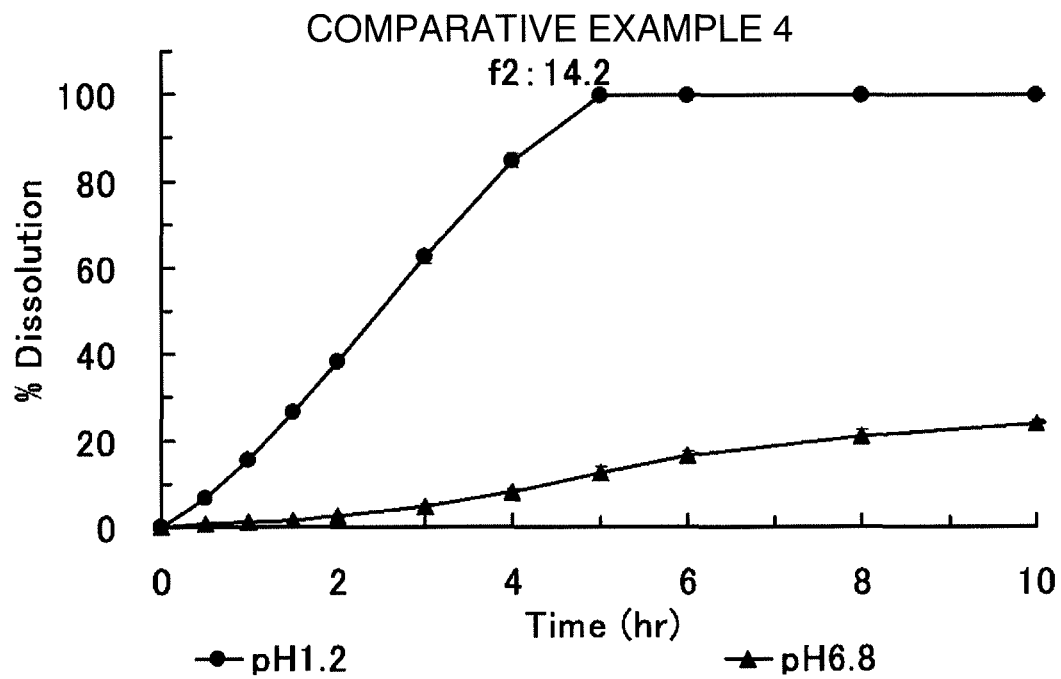
FIG. 5 shows the result of the dissolution test of the sustained release preparation of Comparative Example 4 (Mean±SD, n=3).
Figure 6:
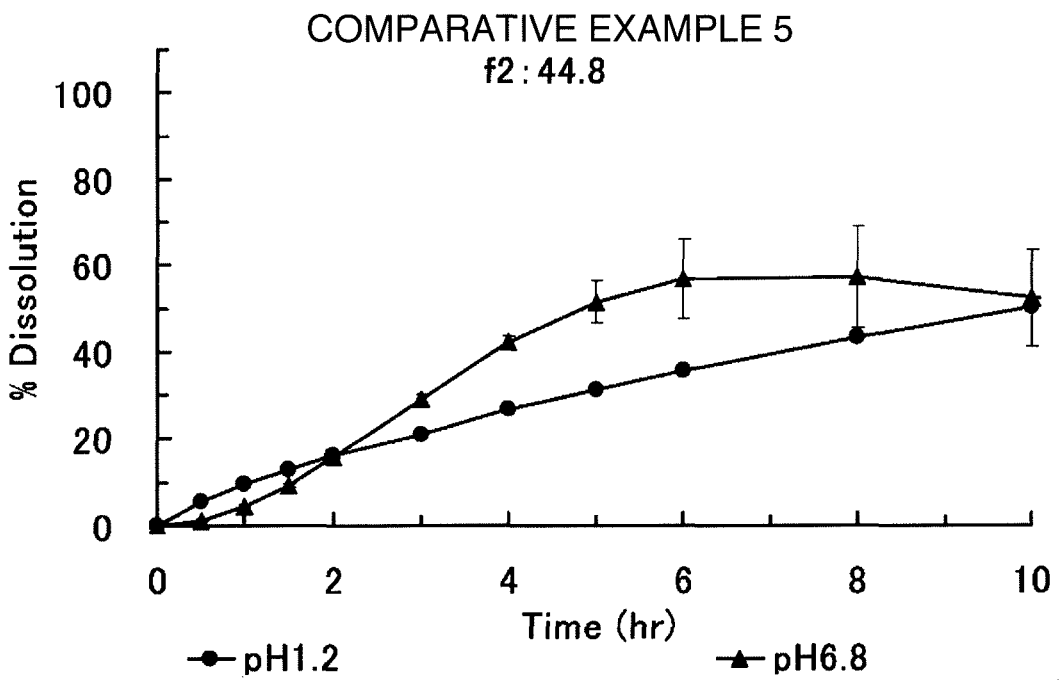
FIG. 6 shows the result of the dissolution test of the sustained release preparation of Comparative Example 5 (Mean±SD, n=3).
Figure 7:
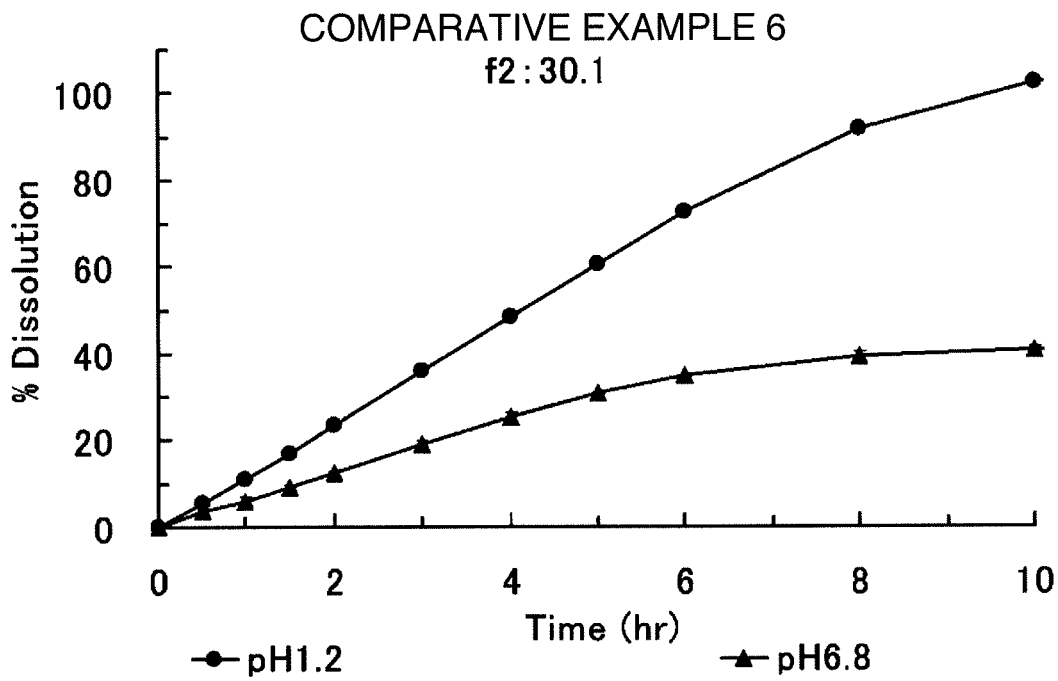
FIG. 7 shows the result of the dissolution test of the sustained release preparation of Comparative Example 6 (Mean±SD, n=3).
Figure 8:
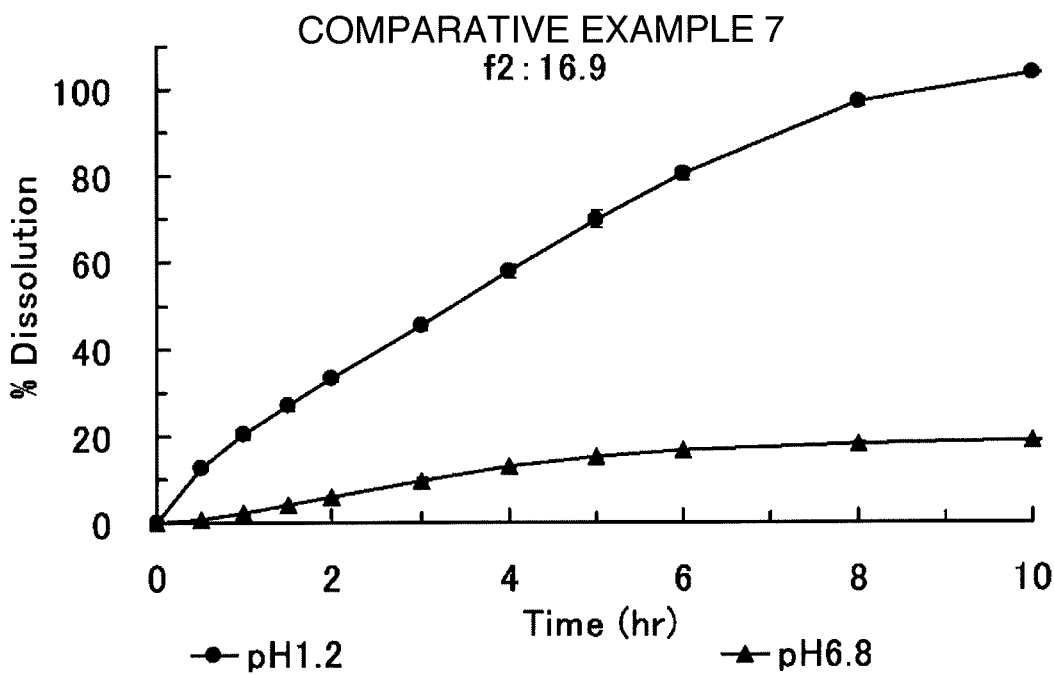
FIG. 8 shows the result of the dissolution test of the sustained release preparation of Comparative Example 7 (Mean±SD, n=3)

The sustained release preparation of the present invention contains a pharmaceutically acceptable salt of compound A, which is an active ingredient. The pharmaceutically acceptable salt of compound A is not particularly limited, but preferably a salt of an inorganic acid, more preferably a salt of a strong inorganic acid, further preferably a hydrochloride, a sulfate or a nitrate, and most preferably a hydrochloride. In addition to the pharmaceutically acceptable salt of compound A, the sustained release preparation of the present invention contains hypromellose as a hydrogel base (which generally denotes a water swelling polymer).

In the present invention, "hypromellose" is synonymous with hydroxypropylmethyl cellulose, which is a mixed ether of methyl ether and hydroxypropyl ether of cellulose. In the present invention, there may be used hypromelloses which have various degrees of substitution as to methoxyl group and hydroxypropoxyl group. Typical examples of hypromellose are substitution degree types of 1828, 2208, 2906 and 2910 (e.g., see the 15th edition of the Japanese Pharmacopoeia, page 887), and any of them can be used for the sustained release preparation of the present invention, but substitution degree type of 2208 or 2910 is preferable. Moreover, hypromelloses having various viscosities can be used, but preferably hypromellose has a viscosity of 50 to 10,000 mPa·s.

In the present invention, hypromellose is contained in the sustained release preparation preferably in an amount of 10 to 90% by mass, more preferably in an amount of 50 to 70% by mass. The amount of hypromellose may vary depending upon the viscosity of the base. For example, when hypromellose has a viscosity of 50 to 100 mPa·s, its amount is preferably 40 to 90% by mass, and when hypromellose has a viscosity of 4,000 to 100,000 mPa·s, its amount is preferably 10 to 40% by mass.

It is preferable that the sustained release preparation of the present invention substantially contains no organic acid. Compound A or a pharmaceutically acceptable salt thereof are quite poor in solubility in water around at a pH range which is similar to enteric environment. Surprisingly, however, the sustained release preparation of the present invention attains desired dissolution and absorbability by not adding such an organic acid as citric acid, tartaric acid, malic acid, fumaric acid, malonic acid, succinic acid and maleic acid, which have been expected to be effective for improving solubility. Herein, "substantially contain no organic acid" means that an organic acid is not contained in such an amount that the above-mentioned compound A or a pharmaceutically acceptable salt thereof is permitted to achieve improved solubility. Though it is preferable that an organic acid is not at all contained, an organic acid may be contained in such a small amount that solubility of compound A or a pharmaceutically acceptable salt thereof is not influenced. When an organic acid is contained in a small amount, the amount is preferably less than 1% by mass, more preferably 0.5% by mass or less, based on the sustained release preparation.

In the present invention, an inert carrier may optionally be added to the sustained release preparation, and can be provided as a granulated medicine, a powdered medicine, an encapsulated medicine, a tablet, etc, by a conventional method. In the present invention, "inert carrier" denotes components other than the hydrogel base which are contained in the preparation together with the medicinal agents but show no medicinal effects. For example, the inert carrier includes an excipient, a lubricant, a disintegrant, a binder, an antioxidant, a coating agent, a colorant, a flavoring substance, a surfactant, a plasticizer, and the like.

As the excipient used in the present invention, for example, there may be used alone or in combination of two or more selected from the group consisting of lactose, crystalline cellulose, sucrose, powdered sugar, granulated sugar, glucose, mannitol, sorbitol, corn starch, starch, gum arabic, dextrin, pullulan, light anhydrous silicic acid, low substituted hydroxypropyl cellulose, sodium carboxymethyl cellulose, synthetic aluminum silicate, and aluminum magnesium metasilicate.

As the lubricant used in the present invention, for example, there may be used alone or in combination of two or more selected from the group consisting of magnesium stearate, calcium stearate, stearic acid, talc, light anhydrous silicic acid, colloidal silica, synthetic aluminum silicate, magnesium aluminometasilicate, calcium hydrogen phosphate, and anhydrous calcium hydrogen phosphate.

Manner of administering the sustained release preparation of the present invention is not particularly limited. In addition to oral administration, parenteral agents such as suppository, aerosol, etc. may be appropriately chosen as necessary. Oral administration is preferable.

The sustained release preparation of the present invention can dissolve compound A independently upon pH while compound A has a solubility dependent upon pH. Therefore, when the preparation is orally administered to a patient, the dissolution rate of the medicinal agent is not changed by properties of digestive fluid in the digestive tract so that variability of the concentration of the medicinal agent in the blood plasma in an individual and between individuals can be minimized.

Moreover, when the preparation is orally administered, $C_{max}$ of compound A can be controlled to an adequate amount. If $C_{max}$ rises to an unnecessary level, risk of occurrence of side effects increases. As a side effect owing to compound A, increase in pulse rate or the like is envisaged. Thus, it is preferable to maintain the concentration in blood plasma in which such a side effect does not occur and only a medicinal effect can be expected.

Furthermore, when the preparation of the present invention is orally administered, effective concentration in blood plasma can be maintained for a long period of time. Since compound A tends to be decomposed by metabolism, it has been expected to be difficult to maintain the concentration in blood plasma for a long period of time by the sustained release preparation of the present invention. Unexpectedly, however, a good absorbability to organism of compound A can be attained according to the present invention.

EXAMPLES

Examples 1-3

The formulation (per tablet) shown in Table 1 was subjected to compression molding by use of a direct tableting method to prepare tablets having a weight of 130 mg/tablet and convex 7 mm in diameter. Herein, METOLOSE 90SH-100SR (Shin-Etsu Chemical Co., Ltd.) having a degree of substitution of 2208 was used as hypromellose, FLOW LAC100 (Meggle Japan Co., Ltd.) was used as lactose hydrate, Adsolider 101 (Freund Corporation) was used as light anhydrous silicic acid, and as magnesium stearate, one manufactured by Taihei Chemical Industrial Co., Ltd. was used.

TABLE 1

| | Blending quantity (mg/tablet) | | |
|---|---|---|---|
| Components | Example 1 | Example 2 | Example 3 |
| Compound A (hydrochloride) | 8 | 8 | 6 |
| Hypromellose (2208, 100 mPa · s) | 72 | 73 | 70 |
| Lactose hydrate | 48 | 47 | 52 |
| Light anhydrous silicic acid | 0.7 | 0.7 | 0.7 |
| Magnesium stearate | 1.3 | 1.3 | 1.3 |
| Total | 130 | 130 | 130 |

Examples 4-6

As shown in Table 2, in the same manner as in Examples 1-3, preparations (tablets) were produced by use of hypromellose except that compression molding was carried out to prepare tablets having flat beveled edge 6 mm in diameter. As hypromellose, METOLOSE 60SH-50 (Shin-Etsu Chemical Co., Ltd.) having a degree of substitution of 2910 was used in Example 4, and METHOCEL K100CR (The Dow Chemical Company) having a degree of substitution of 2208 was used in Examples 5 and 6. As crystalline cellulose, CEOLUS 101 (Asahi Kasei Chemicals Corporation) was used in Example 4 and CEOLUS 301 (Asahi Kasei Chemicals Corporation) was used in Example 5. As lactose hydrate, FLOW LAC 100 (Meggle Japan Co., Ltd.) was used; as dry methacrylic acid copolymer LD, Eudragit L100-55 (Evonik Degussa Japan Co., Ltd.) was used; as light anhydrous silicic acid, AEROSIL 200 (Nippon Aerosil Co., Ltd.) was used; and as magnesium stearate, one manufactured by Taihei Chemical Industrial Co., Ltd. was used.

TABLE 2

| | Blending quantity (mg/tablet) | | |
|---|---|---|---|
| Components | Example 4 | Example 5 | Example 6 |
| Compound A (hydrochloride) | 4 | 4 | 4 |
| Hypromellose (2910, 50 mPa · s) | 50 | — | — |
| Hypromellose (2208, 100 mPa · s) | — | 50 | 30 |
| Crystalline cellulose | 32.5 | 34.5 | — |
| Lactose hydrate | — | — | 54.5 |
| Dry methacrylic acid copolymer LD | 10 | 10 | 10 |
| Light anhydrous silicic acid | 0.5 | 0.5 | 0.5 |
| Magnesium stearate | 1.0 | 1.0 | 1.0 |
| Total | 98 | 100 | 100 |

Comparative Examples 1-4

As shown in Table 3, in the same manner as in Example 1, preparations (tablets) were produced except that hydroxypropyl cellulose, methyl cellulose, pregelatinized starch and polyethylene oxide were used instead of hypromellose used in Examples 1-3. HPC-M (Nippon Soda Co., Ltd.) was used as hydroxypropyl cellulose; METOLOSE SM-100 (Shin-Etsu Chemical Co., Ltd.) was used as methyl cellulose; SWELSTAR MX-1 (Asahi Kasei Chemicals Corporation) was used as pregelatinized starch; and Polyox WSR N750-LEO (The Dow Chemical Company) was used as polyethylene oxide.

TABLE 3

| | Blending quantity (mg/tablet) | | | |
|---|---|---|---|---|
| Components | Comparative Example 1 | Comparative Example 2 | Comparative Example 3 | Comparative Example 4 |
| Compound A (hydrochloride) | 8 | 8 | 8 | 8 |
| Hydroxypropyl cellulose | 72 | — | — | — |
| Methyl cellulose | — | 72 | — | — |
| Pregelatinized starch | — | — | 72 | — |
| Polyethylene oxide | — | — | — | 72 |
| Lactose hydrate | 48 | 48 | 48 | 48 |

TABLE 3-continued

| Components | Blending quantity (mg/tablet) | | | |
|---|---|---|---|---|
| | Comparative Example 1 | Comparative Example 2 | Comparative Example 3 | Comparative Example 4 |
| Light anhydrous silicic acid | 0.7 | 0.7 | 0.7 | 0.7 |
| Magnesium stearate | 1.3 | 1.3 | 1.3 | 1.3 |
| Total | 130 | 130 | 130 | 130 |

Comparative Example 5

As shown in Table 4, in the same manner as in Example 1 except that carboxyvinyl polymer was used instead of hypromellose used in Example 1, a preparation (tablet) was produced. As the carboxyvinyl polymer, CARBOPOL 974P (Lubrizol) was used.

TABLE 4

| Components | Blending quantity (mg/tablet) Comparative Example 5 |
|---|---|
| Compound A (hydrochloride) | 8 |
| Carboxyvinyl polymer | 72 |
| Lactose hydrate | 48 |
| Light anhydrous silicic acid | 0.7 |
| Magnesium stearate | 1.3 |
| Total | 130 |

Comparative Examples 6 and 7

As shown in Table 5, in the same manner as in Example 1, preparations (tablets) were produced except that citric acid hydrate was added in Comparative Example 6, and free compound of compound A was used in Comparative Example 7 instead of the hydrochloride of compound A used in Example 1. The citric acid hydrate was obtained from Iwata Chemical Co., Ltd., pulverized in a mortar, passed through a sieve having opening of 500 μm, and then used.

TABLE 5

| Components | Blending quantity (mg/tablet) | |
|---|---|---|
| | Comparative Example 6 | Comparative Example 7 |
| Compound A (hydrochloride) | 8 | — |
| Compound A (free compound) | — | 7.4 |
| Hypromellose (2208, 100 mPa · s) | 72 | 72 |
| Lactose hydrate | 33 | 48.6 |
| Citric acid hydrate | 15 | — |
| Light anhydrous silicic acid | 0.7 | 0.7 |
| Magnesium stearate | 1.3 | 1.3 |
| Total | 130 | 130 |

Comparative Examples 8 and 9

Normal Tablets

According to the formulation per tablet shown in Table 6, compound A (hydrochloride), crystalline cellulose, citric acid hydrate, hypromellose (METOLOSE TC-5R, Shin-Etsu Chemical Co., Ltd.), and low substituted hydroxypropyl cellulose (LH-31, Shin-Etsu Chemical Co., Ltd.) were mixed and subjected to wet granulation. Furthermore, magnesium stearate was added thereto, and subjected to compression molding to obtain a tablet having a weight of 150 mg and convex 7.5 mm in diameter (Comparative Example 8) and a tablet having a weight of 75 mg and convex 6 mm in diameter (Comparative Example 9). The tablets were subjected to film coating by use of Opadry AMB (Colorcon Japan, LLC) and further subjected to gloss treatment by use of Carnauba wax and light anhydrous silicic acid to obtain normal preparations (tablets).

TABLE 6

(Normal tablet)

| Components | Blending quantity (mg/tablet) | |
|---|---|---|
| | Comparative Example 8 | Comparative Example 9 |
| Compound A (hydrochloride) | 4 | 2 |
| Crystalline cellulose | proper quantity | proper quantity |
| Citric acid hydrate | 15 | 7.5 |
| Hypromellose (2910, 6 mPa · s) | 4.5 | 2.25 |
| Low substituted hydroxypropyl cellulose | 15 | 7.5 |
| Magnesium stearate | 0.6 | 0.3 |
| Opadry AMB | 7.5 | 5.0 |
| Carnauba wax | trace quantity | trace quantity |
| Light anhydrous silicic acid | trace quantity | trace quantity |
| Total | 157.5 | 80.0 |

Examples 7, 8 and Comparative Example 10

As shown in Table 7, in the same manner as in Example 1, preparations (tablets) were produced except that citric acid hydrate was added in Examples 7, 8 and Comparative Example 10. The citric acid hydrate was obtained from Iwata Chemical Co., Ltd., pulverized in a mortar, passed through a sieve having opening of 500 μm, and then used.

TABLE 7

| Components | Blending quantity (mg/tablet) | | |
|---|---|---|---|
| | Example 7 | Example 8 | Comparative Example 10 |
| Compound A (hydrochloride) | 8 | 8 | 8 |
| Hypromellose (2208, 100 mPa · s) | 72 | 72 | 72 |
| Lactose hydrate | 47.87 | 47.35 | 46.7 |
| Citric acid hydrate | 0.13 | 0.65 | 1.3 |
| Light anhydrous silicic acid | 1.3 | 1.3 | 1.3 |
| Magnesium stearate | 0.7 | 0.7 | 0.7 |
| Total | 130 | 130 | 130 |

Comparative Examples 11-15

As shown in Table 8, in the same manner as in Example 1, preparations (tablets) were produced except that tartaric acid, DL-malic acid, fumaric acid, succinic acid or maleic acid was added. The tartaric acid was obtained from Dainippon Sumitomo Pharma Co., Ltd., DL-malic acid was obtained from Fuso Chemical Co., Ltd., fumaric acid and succinic acid were obtained from Nippon Shokubai Co., Ltd., and maleic acid was obtained from Wako Pure Chemical Industries, Ltd. Each of these acids was pulverized in a mortar, passed through a sieve having opening of 500 μm, and then used.

TABLE 8

| Components | Blending quantity (mg/tablet) | | | | |
| --- | --- | --- | --- | --- | --- |
| | Comparative Example 11 | Comparative Example 12 | Comparative Example 13 | Comparative Example 14 | Comparative Example 15 |
| Compound A (hydrochloride) | 8 | 8 | 8 | 8 | 8 |
| Hypromellose (2208, 100 mPa·s) | 72 | 72 | 72 | 72 | 72 |
| Lactose hydrate | 35 | 35 | 35 | 35 | 35 |
| Tartaric acid | 13 | — | — | — | — |
| DL-malic acid | — | 13 | — | — | — |
| Fumaric acid | — | — | 13 | — | — |
| Succinic acid | — | — | — | 13 | — |
| Maleic acid | — | — | — | — | 13 |
| Light anhydrous silicic acid | 1.3 | 1.3 | 1.3 | 1.3 | 1.3 |
| Magnesium stearate | 0.7 | 0.7 | 0.7 | 0.7 | 0.7 |
| Total | 130 | 130 | 130 | 130 | 130 |

Examples 9-11

As shown in Table 9, in the same manner as in Example 1, preparations (tablets) were produced except that the quantities of hypromellose were changed in Examples 9-11.

TABLE 9

| Components | Blending quantity (mg/tablet) | | |
| --- | --- | --- | --- |
| | Example 9 | Example 10 | Example 11 |
| Compound A (hydrochloride) | 8 | 8 | 8 |
| Hypromellose (2208, 100 mPa·s) | 58.5 | 91 | 97.5 |
| Lactose hydrate | 61.5 | 29 | 22.5 |
| Light anhydrous silicic acid | 1.3 | 1.3 | 1.3 |
| Magnesium stearate | 0.7 | 0.7 | 0.7 |
| Total | 130 | 130 | 130 |

Examples 12-14

As shown in Table 10, in the same manner as in Example 1, preparations (tablets) were produced except that the substitution type, viscosity and quantity of hypromellose were changed in Examples 12-14. As hypromellose, METOLOSE 60SH-50 having a degree of substitution of 2910 (Shin-Etsu Chemical Co., Ltd.) was used in Example 12; METOLOSE 65SH-4000 having a degree of substitution of 2906 (Shin-Etsu Chemical Co., Ltd.) was used in Example 13; and METOLOSE 90SH-100000SR having a degree of substitution of 2208 (Shin-Etsu Chemical Co., Ltd.) was used in Example 14.

TABLE 10

| Components | Blending quantity (mg/tablet) | | |
| --- | --- | --- | --- |
| | Example 12 | Example 13 | Example 14 |
| Compound A (hydrochloride) | 8 | 8 | 8 |
| Hypromellose (2910, 50 mPa·s) | 117 | — | — |
| Hypromellose (2906, 4000 mPa·s) | — | 19.5 | — |
| Hypromellose (2208, 100000 mPa·s) | — | — | 13 |
| Lactose hydrate | 3 | 100.5 | 107 |

TABLE 10-continued

| Components | Blending quantity (mg/tablet) | | |
| --- | --- | --- | --- |
| | Example 12 | Example 13 | Example 14 |
| Light anhydrous silicic acid | 1.3 | 1.3 | 1.3 |
| Magnesium stearate | 0.7 | 0.7 | 0.7 |
| Total | 130 | 130 | 130 |

Test Example 1

Dissolution Test

The dissolution test was conducted according to the 15th edition of the Japanese Pharmacopoeia, method 2 (paddle method). As the test liquid, liquid 1 (pH: 1.2) and liquid 2 (pH: 6.8) prescribed in the 15th edition of the Japanese Pharmacopoeia were used each in an amount of 900 mL. In the test, a sinker was used, and the test was conducted at a paddle rotating velocity of 50 rpm and at a temperature of 37° C.

In the present invention, judgment on whether dissolution of the sustained release preparation is dependent or independent upon pH was conducted by reference to Yakushokushinsa, No. 1124004 issued on Nov. 24, 2006 by Director, Evaluation and Licensing Division, Pharmaceutical and Food Safety Bureau, Ministry of Health and Welfare "Guideline for Bioequivalency Test of Generic Drugs". In particular, when dissolution behavior in the liquid 1 and liquid 2 of one preparation satisfy "Similarity judgment standard" described below, the dissolution of the sustained release preparation was judged as pH independent.

(Similarity Judgment Standard)

a. When the average dissolution rate of liquid 1 of the preparation becomes 80% or higher after 20 hours from the start of the dissolution test, f2 value is 42 or more.

b. When the average dissolution rate of liquid 1 of the preparation becomes 50% or higher but less than 80% after 20 hours from the start of the dissolution test, f2 value is 46 or more.

c. When the average dissolution rate of liquid 1 of the preparation does not reach 50% after 20 hours from the start of the dissolution test, f2 value is 53 or more.

Herein, the f2 value is represented by the following formula $$f_2 = 50 \log \left[ \frac{100}{\sqrt{1 + \frac{\sum_{i=1}^{n}(Ti - Ri)^2}{n}}} \right]$$

wherein Ti is the average dissolution rate of liquid 2 of the preparation and Ri is the average dissolution rate of liquid 1 of the preparation at the time of comparing the average dissolution rate, and n is the number of time points in which the average dissolution rate is compared.

The time points in which the average dissolution rate is compared were determined by the following standard.
(1) When the average dissolution rate of liquid 1 becomes 80% or higher after 15 minutes to 30 minutes from the start of the dissolution test, the time points are 15 minutes, 30 minutes and 45 minutes.
(2) When the average dissolution rate of liquid 1 becomes 80% or higher after 30 minutes to 20 hours from the start of the dissolution test, the time points are Ta/4, 2Ta/4, 3Ta/4 and Ta wherein Ta is an appropriate time point in which the average dissolution rate of liquid 1 becomes 80%.
(3) When the average dissolution rate of liquid 1 of the preparation does not reach 80% after 20 hours from the start of the dissolution test, the time points are Ta/4, 2Ta/4, 3Ta/4 and Ta wherein Ta is an appropriate time point in which the average dissolution rate of liquid 1 becomes 80% of that measured after 20 hours from the start of the dissolution test of liquid 1.

For example, for the preparation of Example 1 shown in FIG. 1, the similarity judgment standard "a" was adopted, because the average dissolution rate of liquid 1 of the preparation was 80% or higher after 20 hours from the start of the dissolution test. Moreover, because the time point in which the average dissolution rate of liquid 1 of the preparation reached 80% was after 6 hours from the start of the dissolution test (Ta=6 hours), the time points in which the average dissolution rate was compared were four points of 1.5, 3, 4.5 6 hours and f2 value was calculated.

FIGS. 1-12 show the results up to 10 hours after the start of the dissolution tests.

As shown in FIG. 1, in the preparation of Example 1, immediate dissolution of compound A was suppressed and stable zero-order release was attained. Because difference was hardly recognized between liquid 1 and liquid 2 in the dissolution rate of compound A, and the f2 value was 42 or more, it was found that the dissolution was independent upon pH.

Figure 9:
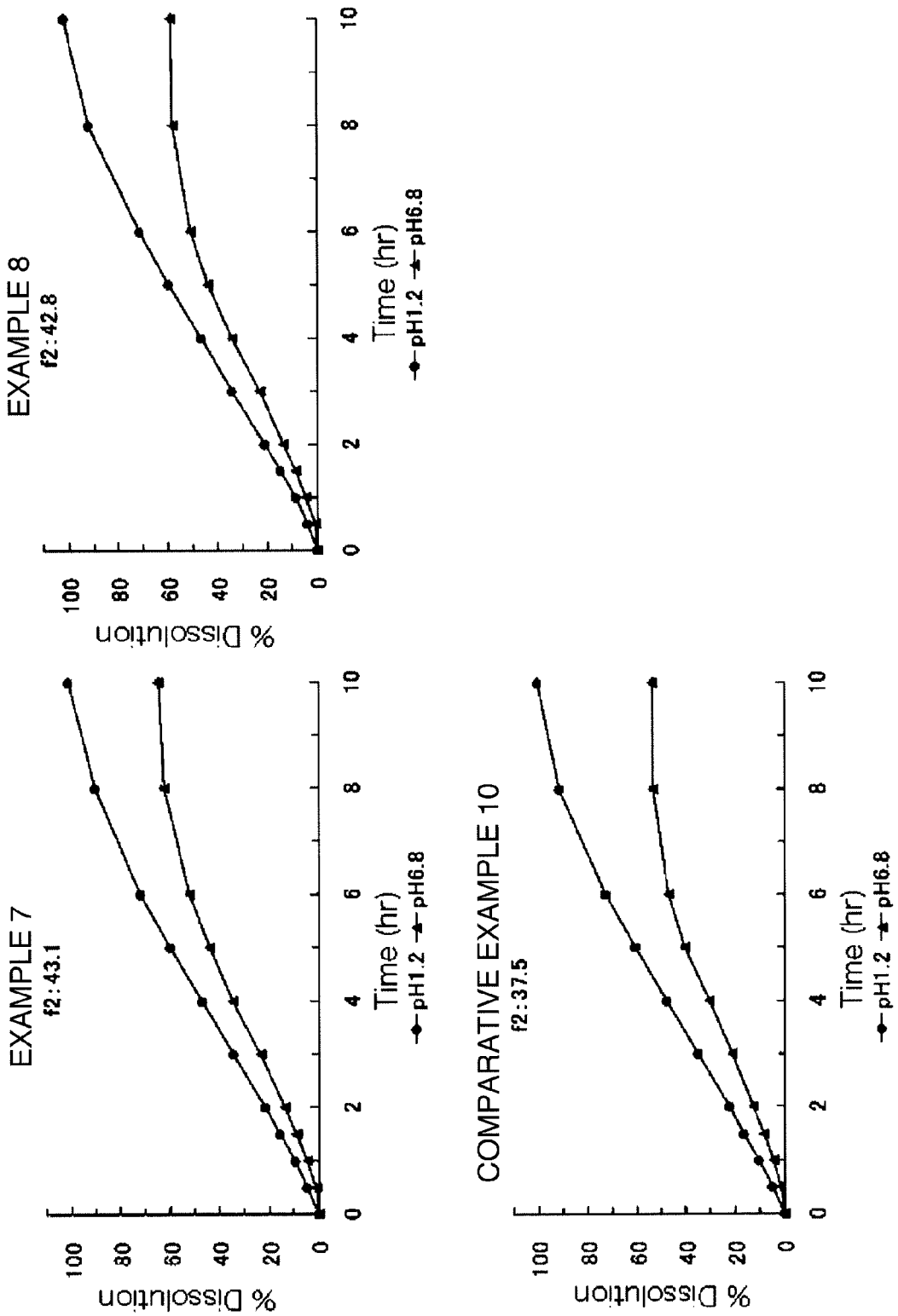
FIG. 9 shows the result of the dissolution test of the sustained release preparations of Example 7, Example 8 and Comparative Example 10 (Mean±SD, n=3).

As shown in FIG. 9, in the preparations of Examples 7 and 8, immediate dissolution of compound A was suppressed and stable zero-order release was attained. Because difference was hardly recognized between liquid 1 and liquid 2 in the dissolution rate of compound A, and the f2 value was 42 or more, it was found that the dissolution was independent upon pH.

Figure 11:
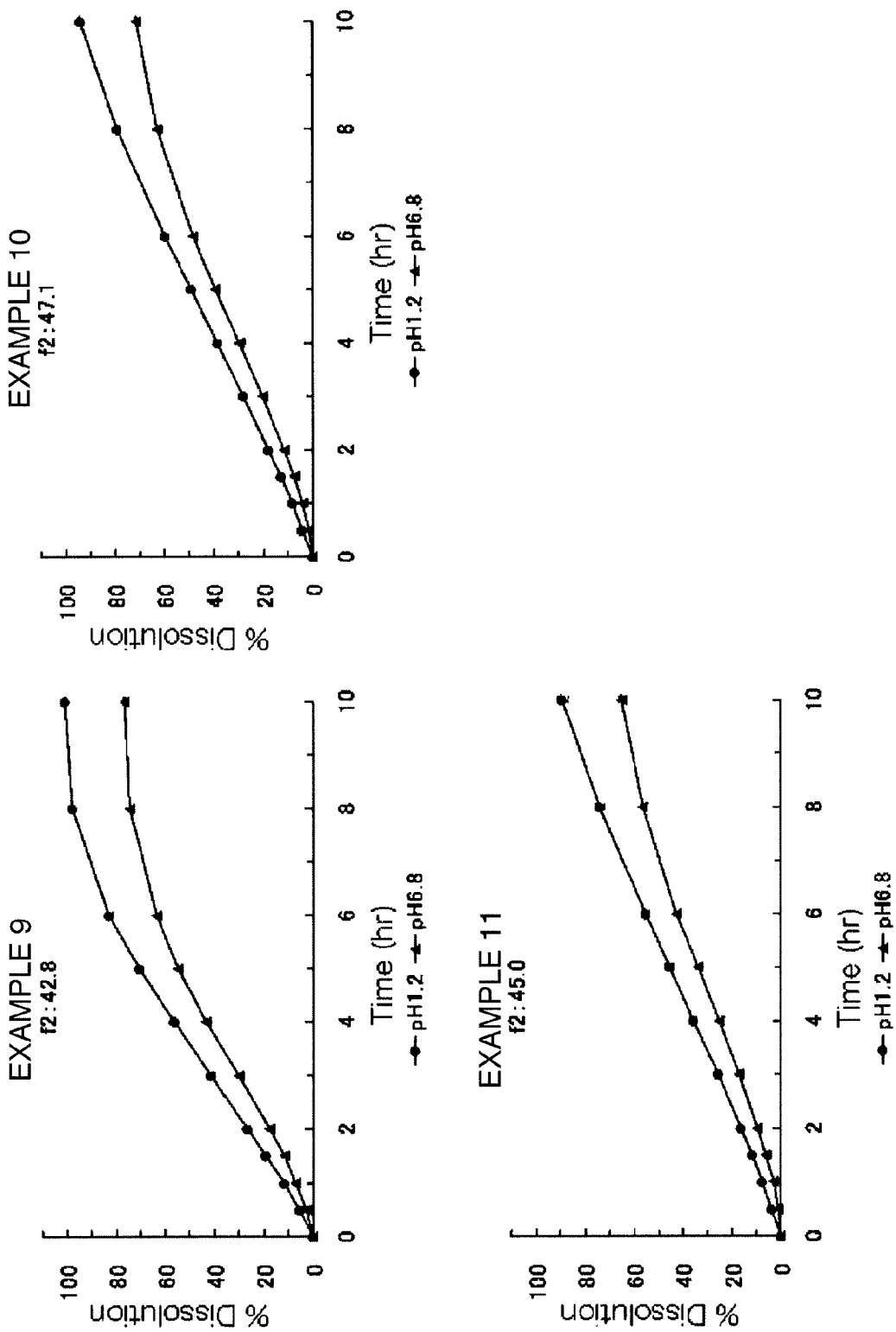
FIG. 11 shows the result of the dissolution test of the sustained release preparations of Examples 9-11 (Mean±SD, n=3).

As shown in FIG. 11, in the preparations of Examples 9, 10 and 11, immediate dissolution of compound A was suppressed and stable zero-order release was attained. Because difference was hardly recognized between liquid 1 and liquid 2 in the dissolution rate of compound A, and the f2 value was 42 or more, it was found that the dissolution was independent upon pH.

Figure 12:
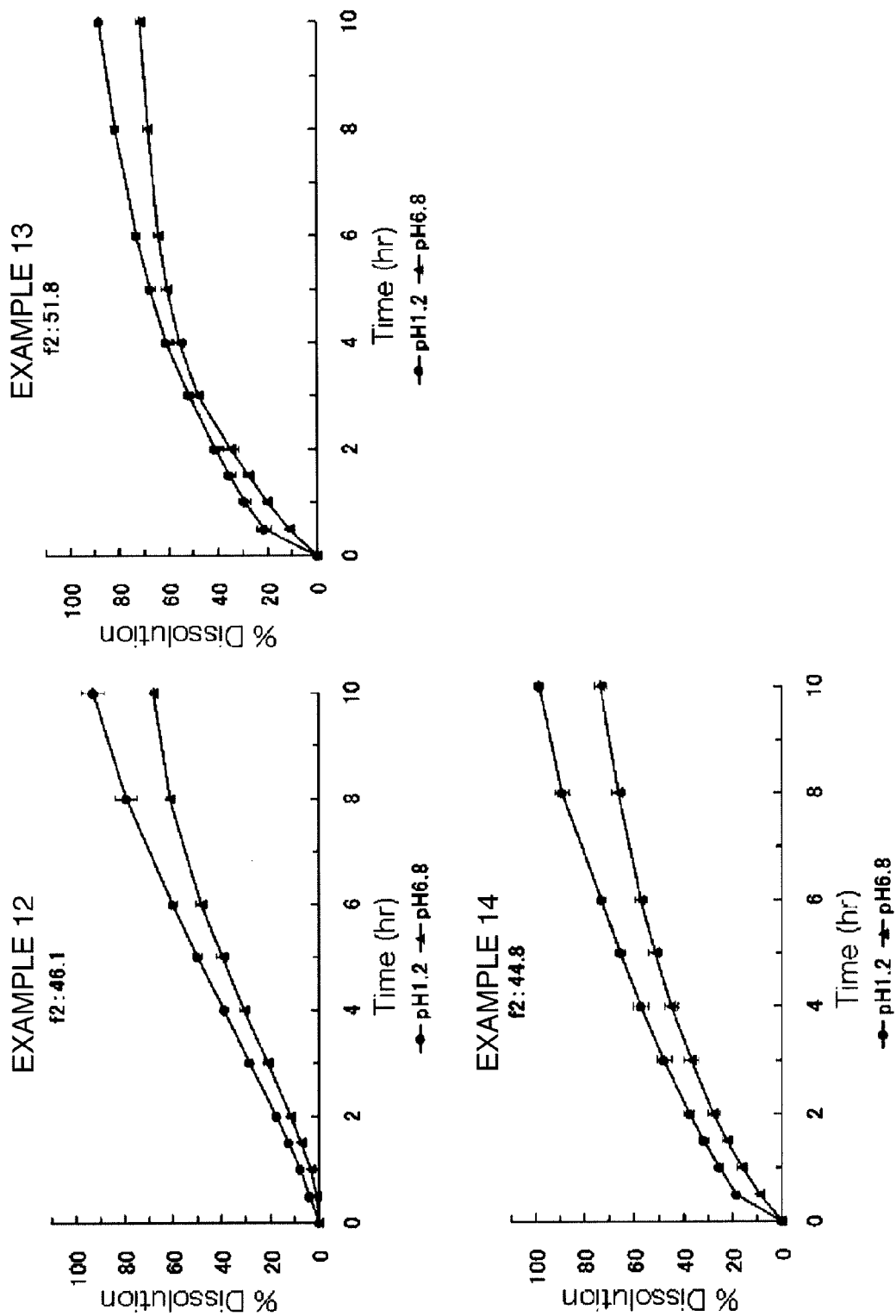
FIG. 12 shows the result of the dissolution test of the sustained release preparations of Examples 12-14 (Mean±SD, n=3).

As shown in FIG. 12, in the preparations of Examples 12, 13 and 14, immediate dissolution of compound A was suppressed and stable zero-order or primary release was attained. Because difference was hardly recognized between liquid 1 and liquid 2 in the dissolution rate of compound A, and the f2 value was 42 or more, it was found that the dissolution was independent upon pH.

In the preparation of Comparative Example 2 shown in FIG. 3, immediate dissolution could not be suppressed. Moreover, the f2 value by which pH dependency was judged could not be calculated.

As shown in FIGS. 2 and 4-8, in the preparations of Comparative Examples 1, 3, 4, 5, 6 and 7, sustained release was attained but the f2 values were below the standard (less than 42 in Comparative Examples 1, 4, 6 and 7, less than 46 in Comparative Examples 3 and 5), and hence it was found that the dissolution was highly dependent upon pH.

As shown in FIG. 9, in the preparation of Comparative Example 10, sustained release was attained but the C value was less than 42, and hence it was found that the dissolution was highly dependent upon pH.

Figure 10:
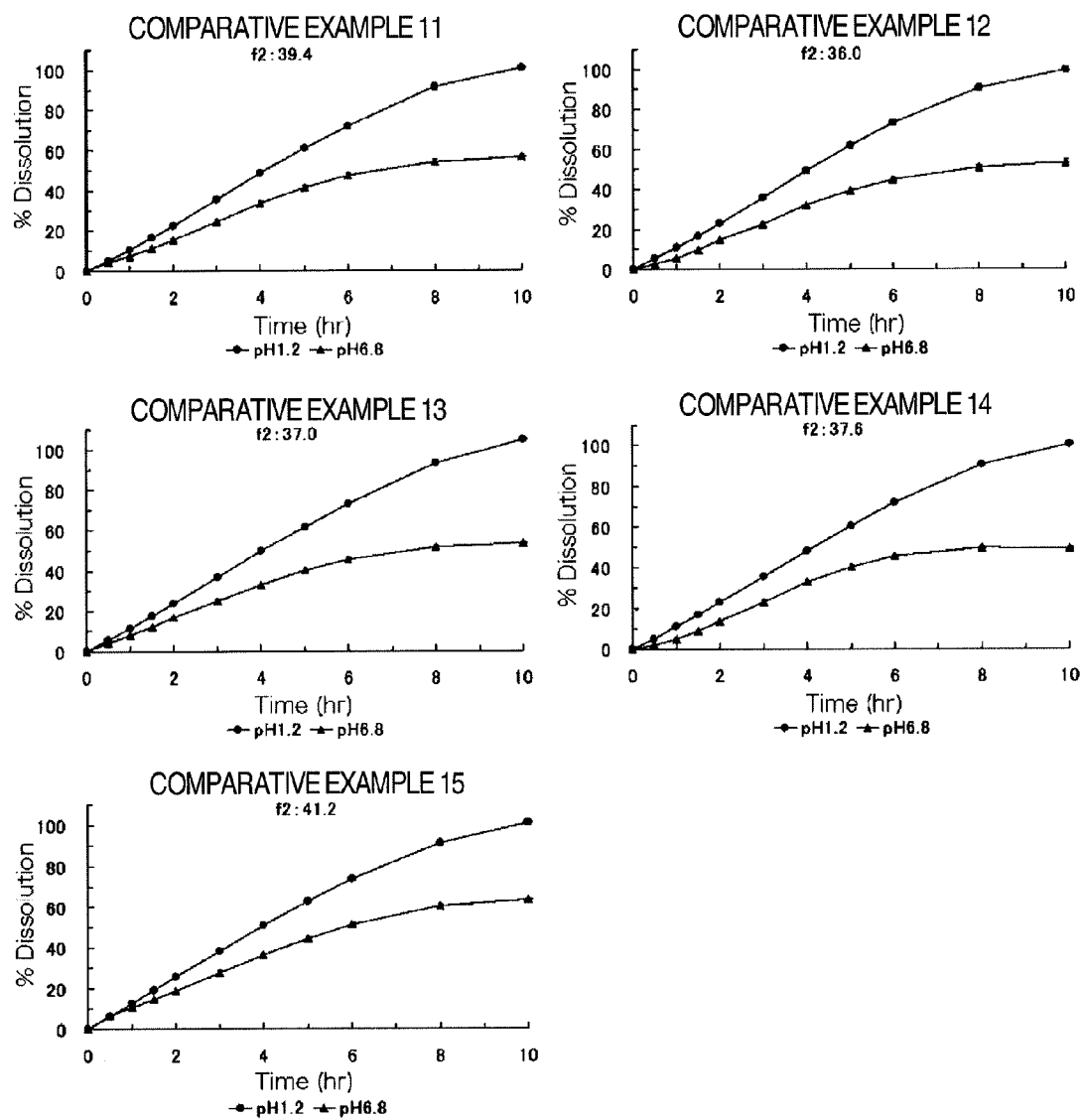
FIG. 10 shows the result of the dissolution test of the sustained release preparations of Comparative Examples 11-15 (Mean±SD, n=3).

As shown in FIG. 10, in the preparations of Comparative Examples 11, 12, 13, 14 and 15, sustained release was attained but the C values were all less than 42, and hence it was found that the dissolution was highly dependent upon pH.

Test Example 2

Dog BA Test 1

To each of eight (8) beagle dogs which had been deprived of food for 16 hours, a tablet of the preparation of Example 2 or Example 3 or the normal preparation of Comparative Example 8 was orally administered. After the administration, blood was collected from a cutaneous vein on the radial side of a forelimb and subjected to centrifugal separation. The concentration of compound A (free compound) in the blood plasma was measured by an LC/MS/MS method using a mass spectrometer, AP14000 (manufactured by Applied Biosystems/MDS SCIEX). Furthermore, pharmacokinetic parameters, $C_{max}$ and $T_{max}$, obtained by pharmacokinetic analysis, and area under a curve of the concentration in blood plasma–time (AUC) were calculated and shown in Table 11. Relative bioavailability (Relative BA) was calculated using Comparative Example 8 as a control, from ratios of AUC of Examples 2 and 3 to AUC of Comparative Example 8, further on the assumption that dosages were the same as one another.

Figure 13:
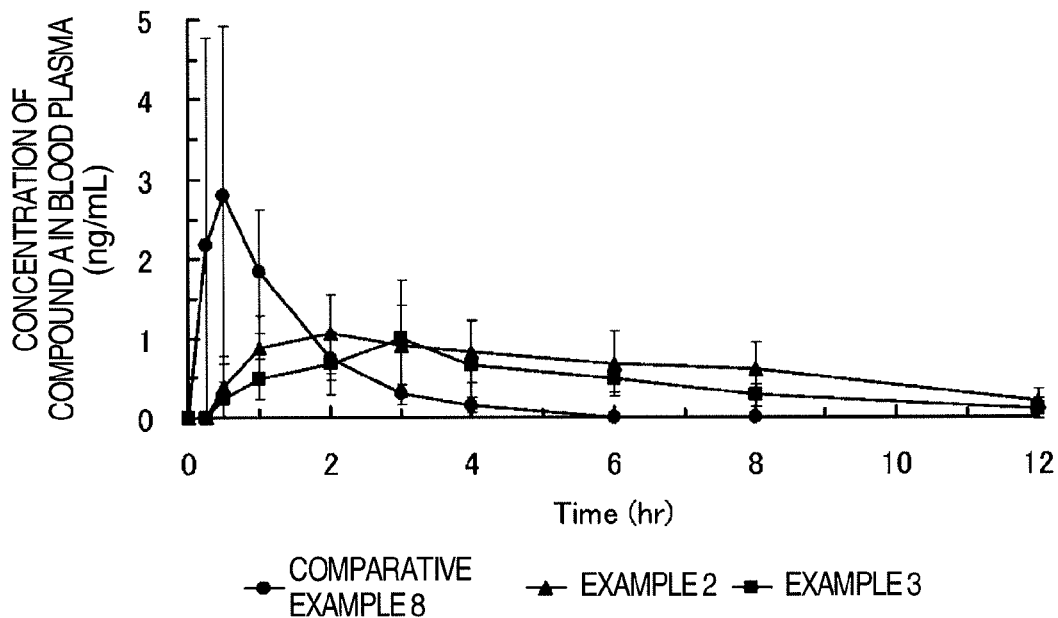
FIG. 13 shows the profile of the concentration in blood plasma of compound A upon oral administration to a dog of the sustained release preparation of Example 2 or 3, or the ordinary preparation of Comparative Example 8 (Mean±SD, n=8).

From FIG. 13 and Table 11, it is found that, compared with the normal tablet of Comparative Example 8, the sustained release tablets of Examples reduces $C_{max}$ without decreasing AUC, and maintain the concentration in blood plasma for a long period of time.

TABLE 11

| Dosing preparation | Dosage (mg/dog) | $C_{max}$ (ng/mL) | $T_{max}$ (hr) | AUC (ng · hr/mL) | Relative BA (%) |
|---|---|---|---|---|---|
| Comparative Example 8 | 4 | 3.34 ± 2.05 | 0.688 ± 0.579 | 4.16 ± 1.74 | 100 |
| Example 2 | 8 | 1.35 ± 0.346 | 2.69 ± 1.75 | 7.54 ± 2.51 | 90.6 |
| Example 3 | 6 | 1.23 ± 0.597 | 1.88 ± 1.09 | 5.21 ± 1.35 | 83.5 |

Test Example 3

Dog BA Test 2

Figure 14:
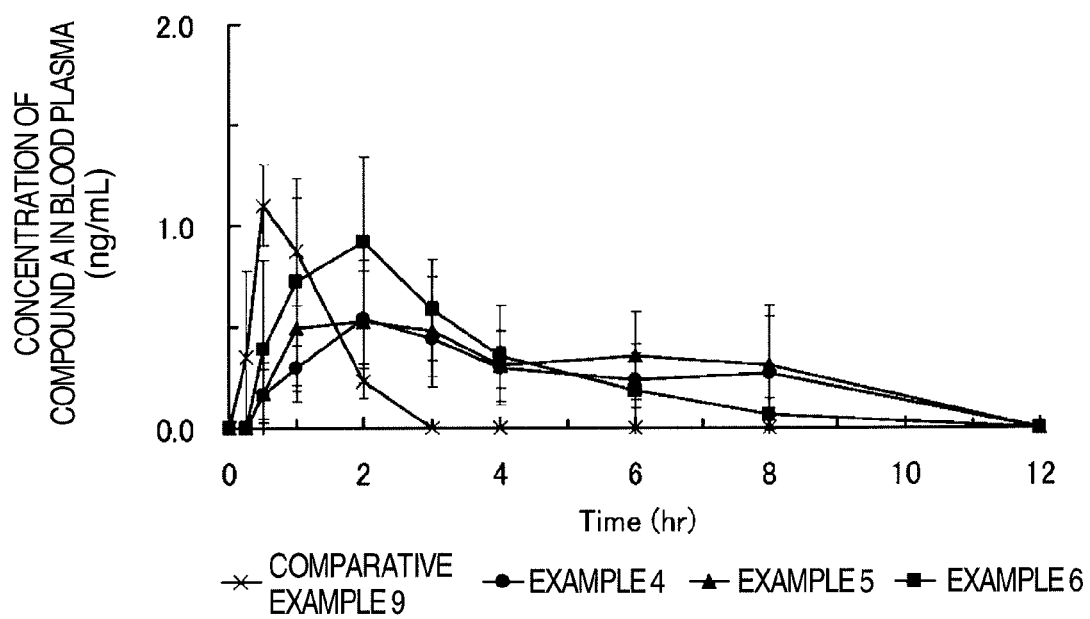
FIG. 14 shows the profile of the concentration in blood plasma of compound A upon oral administration to a dog of the sustained release preparation of Example 4, 5 or 6, or the ordinary preparation of Comparative Example 9 (Mean±SD, n=8).

In the same manner as in Test Example 2, a normal tablet of Comparative Example 9, and each one tablet of sustained release preparations of Examples 4, 5 and 6 were orally administered. Profiles of concentrations in blood plasma are shown in FIG. 14 and pharmacokinetic parameters are shown in Table 12. From FIG. 14 and Table 12, it is found that, compared with the normal tablet of Comparative Example 9, the sustained release tablets of Examples reduce $C_{max}$ without decreasing AUC, and maintain the concentration in blood plasma for a long period of time.

TABLE 12

| Dosing preparation | Dosage (mg/dog) | $C_{max}$ (ng/mL) | $T_{max}$ (hr) | AUC (ng · hr/mL) | Relative BA (%) |
|---|---|---|---|---|---|
| Comparative Example 9 | 2 | 1.18 ± 0.141 | 0.656 ± 0.297 | 1.34 ± 0.220 | 100 |
| Example 4 | 4 | 0.671 ± 0.237 | 2.88 ± 2.17 | 2.93 ± 1.21 | 109.3 |
| Example 5 | 4 | 0.669 ± 0.318 | 2.81 ± 2.17 | 3.56 ± 1.98 | 132.8 |
| Example 6 | 4 | 1.07 ± 0.350 | 2.00 ± 1.07 | 3.02 ± 1.72 | 112.7 |

INDUSTRIAL APPLICABILITY

According to the present invention, it becomes possible to provide a sustained release preparation that can dissolve a medicinal agent independently upon pH while the medicinal agent has a solubility dependent upon pH. Moreover, upon oral administration, it becomes possible to provide a sustained release preparation that can reduce the maximum concentration in blood plasma of a medicinal agent and can maintain effective concentration of the medicinal agent in the blood plasma for a long period of time as compared with ordinary preparations.

The invention claimed is:

1. A sustained release preparation characterized in that the sustained release preparation contains a pharmaceutically acceptable salt of 4-bromo-6-[3-(4-chlorophenyl)propoxy]-5-(3-pyridylmethylamino)-3(2H)-pyridazinone and hypromellose, and an organic acid is blended in the sustained release preparation in an amount of 0.5% by mass or less; wherein the hypromellose is contained in the sustained release preparation in an amount of 10 to 90% by mass.

2. A sustained release preparation according to claim 1, characterized by further containing a pharmaceutically acceptable inert carrier.

3. A sustained release preparation according to claim 1, characterized in that the pharmaceutically acceptable salt of 4-bromo-6-[3-(4-chlorophenyl)propoxy]-5-(3-pyridylmethylamino)-3(2H)-pyridazinone is a hydrochloride.

4. A sustained release preparation according to claim 1, characterized in that no organic acid is present.

* * * * *

UNITED STATES PATENT AND TRADEMARK OFFICE
CERTIFICATE OF CORRECTION

PATENT NO. : 8,912,192 B2  
APPLICATION NO. : 13/578323  
DATED : December 16, 2014  
INVENTOR(S) : Noriyuki Hirasawa et al.

Page 1 of 1

It is certified that error appears in the above-identified patent and that said Letters Patent is hereby corrected as shown below:

On the Title Page, Column 1,

"(87)    PCT Pub. No.:  WO2011/009573

PCT Pub. Date: Aug. 18, 2011", should be

--(87)    PCT Pub. No.:  WO2011/099573

PCT Pub. Date: Aug. 18, 2011--.

Signed and Sealed this  
Twenty-first Day of June, 2016

Michelle K. Lee  
*Director of the United States Patent and Trademark Office*